United States Patent [19]

Noguchi

[11] Patent Number: 4,898,175
[45] Date of Patent: Feb. 6, 1990

[54] OUT-BODY OBSERVING APPARATUS

[75] Inventor: Toshiaki Noguchi, Tachikawa, Japan

[73] Assignee: Olympus Optical Co., Ltd., Tokyo, Japan

[21] Appl. No.: 137,215

[22] Filed: Dec. 22, 1987

[30] Foreign Application Priority Data

Dec. 26, 1986 [JP] Japan .................. 61-313273

[51] Int. Cl.$^4$ .............................................. A61B 5/00
[52] U.S. Cl. ......................................... 128/634; 128/6; 128/664
[58] Field of Search ............................ 128/664, 634, 6

[56] References Cited

U.S. PATENT DOCUMENTS

| 4,541,438 | 9/1985  | Parker et al.    | 128/664 |
| 4,556,057 | 12/1985 | Hiruma et al.    | 128/634 |
| 4,576,173 | 3/1986  | Parker et al.    | 128/664 |
| 4,592,361 | 6/1986  | Parker et al.    | 128/664 |
| 4,631,582 | 12/1986 | Nagasaki et al.  | 128/6   |
| 4,697,593 | 10/1987 | Enons et al.     | 128/634 |
| 4,776,340 | 10/1988 | Moran et al.     | 128/634 |

FOREIGN PATENT DOCUMENTS

| 0252578 | 1/1988  | European Pat. Off. ............ 128/634 |
| 3436057 | 12/1985 | Fed. Rep. of Germany . |
| 5421678 | 4/1987  | Japan . |

Primary Examiner—A. Michael Chambers
Attorney, Agent, or Firm—Armstrong, Nikaido, Marmelstein, Kubovcik & Murray

[57] ABSTRACT

In this out-body observing apparatus, an illuminating light fed by an illuminating device is emitted from the tip part of an insertable part of an endoscope inserted into a body cavity and is radiated onto a part to be observed. This illuminating light having passed through a living body tissue is imaged by an imaging device provided outside the body. This imaging means delivers a picture image signal to a signal processing device. This signal processing device processes the signal and outputs a video signal to a displaying device. This displaying device displays on a picture surface the image of the observed part of the tissue within the living body.

30 Claims, 4 Drawing Sheets

OUT-BODY OBSERVING APPARATUS

FIELD OF THE INVENTION

This invention relates to an out-body observing apparatus whereby an illuminating light is directed outward of a body from within the body so as to be able to be utilized to observe a tissue interior through which the light has passed.

BACKGROUND OF THE INVENTION

Recently, there has come to be extensively used an endoscope whereby an elongated insertable part can be inserted into a body cavity to observe an internal organ or the like within the body cavity or to make any curing treatment by using a treating tool inserted through a treating tool channel as required.

In the conventional endoscope, for example, an illuminating light emitted from a light source device outside a body is led into the body cavity through a light guide inserted through an insertable part and is radiated onto a tissue within the body cavity, the light reflected from the surface of the tissue is received and observed with the naked eye in an eyepiece part or is imaged by a television camera or the like to observe the tissue surface within the body cavity.

However, with such a conventional endoscope, the tissue interior state as, for example, the blood flowing state in the veins below the mucous membrane of the stomach or the minute structure of the vein has been substantially unable to be observed. Therefore, in the diagnosis or the like of a disease of the tissue interior, tissue has had to be collected by using a forceps, again analyzed in detail, examined and diagnosed. In such a diagnosis, it takes a very long time until the result of the diagnosis is made known and the result of the diagnosis by a presumption to some extent can not help being made known. The unrest given to the patient will be large, the diagnosing time will be long and the tissue taking position will hurt. These are various problems.

In the patent gazette of Japanese Patent Publication No. 21678/1979, there is disclosed a technique wherein an image is formed, within an imaging mechanism provided in an endoscope, by an illuminating light having passed through a tissue from outside a body so that a deep part of the wall within the body may be observed.

Also, in USP 4541438, there is disclosed a technique of detecting the presence of a cancer with a fluorescence comprising an induced light radiating means, an optical detecting means detecting a fluorescence emitted by a specific tumor marker and a displaying means operatively connected with the detecting means.

However, there are disadvantages that, in the case of the observation by inserting the imaging means in the above mentioned prior art examples, the size of the imaging means will be limited and the operation will be difficult.

OBJECT AND SUMMARY OF THE INVENTION

An object of the present invention is to provide an out-body observing apparatus whereby a tissue interior can be easily observed from outside a body.

The present invention is to provide an imaging device whereby an illuminating light is radiated by an illuminating device from within a body onto a part to be observed within the body and a tissue interior is observed with the light emitted from the above mentioned illuminating device and having passed through the living body tissue.

The other features and advantages of the present invention will become apparent enough with the following explanation.

BRIEF DESCRIPTION OF THE DRAWINGS

FIG. 1 is an explanatory view showing the formation of an out-body observing apparatus.

FIG. 2 is an explanatory view showing a tip part of an endoscope.

DETAILED DESCRIPTION OF PREFERRED EMBODIMENTS

The embodiments of the present invention shall be concretely explained in the following with reference to the drawings.

Figure 1:
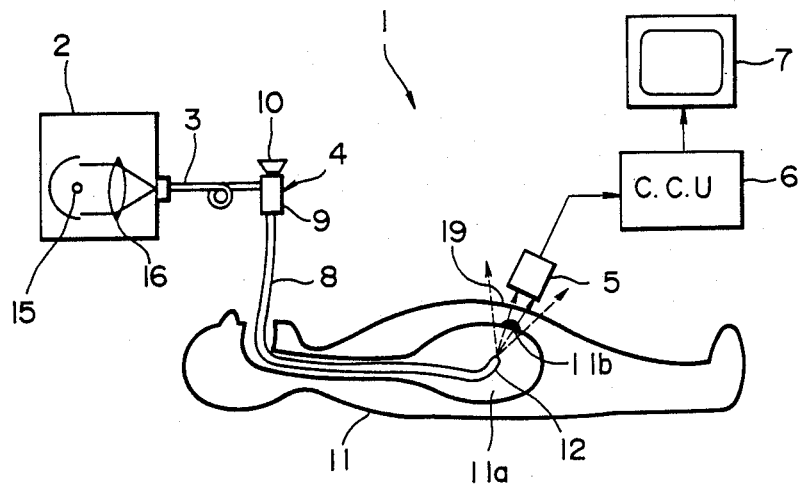
FIGS. 1 and 2 relate to the first embodiment of the present invention.
Figure 2:
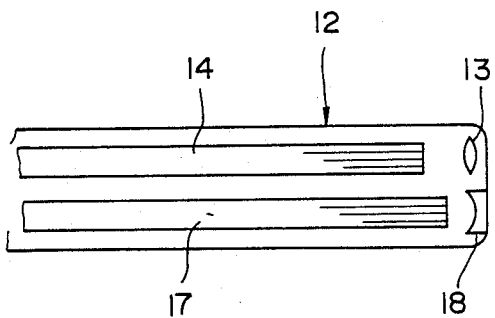

FIGS. 1 and 2 relate to the first embodiment of the present invention. FIG. 1 is an explanatory view showing the formation of an out-body observing apparatus. FIG. 2 is an explanatory view showing a tip part of an endoscope.

As shown in FIG. 1, an out-body observing apparatus 1 of this embodiment comprises a light source device 2 as an illuminating means, an endoscope 4 connected to this light source device 2 through a cable 3, an imaging part 5 as an imaging means provided outside a body, a camera controlling unit 6 controlling this imaging part 5 and processing a video signal and a monitor 7 as a displaying means connected to the above mentioned camera controlling unit 6.

The above mentioned endoscope 4 is formed of an elongated insertable part 8, a thick operating part 9 connected to the rear end of this insertable part 8 and an eyepiece part 10 provided at the rear end of this operating part 9. The above mentioned insertable part 8 may be either flexible or rigid and can be inserted into a cavity 11a of a human body 11. As shown in FIG. 2, an image forming optical system 13 consisting of an objective lens system or the like is provided in the tip part 12 of this insertable part 8 and the tip surface of an image guide 14 formed of a flexible fiber bundle inserted through the above mentioned insertable part 8 is arranged in the image forming position of this image forming optical system 13 so that an observed image formed on the tip surface of this image guide 14 may be led to the operating part by this image guide 14 and observed by the above mentioned eyepiece part 10.

The above mentioned light source device 2 is provided with a lamp 15 so that the light emitted from this lamp 15 may be condensed by a condenser 16 or the like and may enter a light guide 17 formed of a flexible fiber bundle. This light guide 17 is inserted through the above mentioned cable 3 and insertable part 8 so that the illuminating light entering this light guide 17 may be emitted from the exit end of this light guide 17 and may be radiated outward of a body onto a part 11b to be observed within the body cavity 11 through a light distributing lens 18. The illuminating light radiated onto this part 11b to be observed is to come out of the body through a tissue of the living body.

For the lamp 15 of the above mentioned light source device may be used a xenone lamp, halogen lamp, strobe lamp, LED or EL (Electro Luminance). The wavelength range of the emitted light may be of one, two or all of an ultraviolet range, visible range and infrared range.

On the other hand, the above mentioned imaging part 5 is arranged near the body surface 19 so as to be opposed to the observed part 11b illuminated by the illuminating light emitted from the above mentioned endoscope tip part 12 and to image the projected image of the living body tissue by the above mentioned illuminating light having come out of the body through the tissue. This imaging part 5 comprises, for example, an imaging forming optical system and such solid state imaging device or imaging tube as a CCD having a sensitivity to such desired wavelength range as of infrared rays and arranged in the image forming position of this image forming optical system. The output signal of this imaging part 5 is input into the above mentioned camera controlling unit 6, is processed in this camera controlling unit 6 to be converted to an image signal and is then input into a monitor 7 to display the observed image.

In case another external irregular light than the light having passed through the living body tissue enters the above mentioned imaging part 5, the projected image of the living body tissue will be hard to observe. Therefore, the above mentioned imaging part 5 may be provided with a light intercepting means or may be made dark on the periphery to prevent the external irregular light.

In this embodiment of a formation as in the above, the light emitted from the light source device 2 is led into the body cavity 11a by the light guide 17, is emitted from the exit end of this light guide 17 and is radiated outward of the body onto the part 11b to be observed within the cavity 11a through the light distributing lens 18. This illuminating light reaches the outside of the body through the living body tissue. The projected image of the living body tissue by the light having passed through the living body tissue is imaged by the imaging part 5.

Thus, according to this embodiment, as the projected image of the living body tissue by the light having passed through the living body tissue can be observed, the information of such tissue interior state as for example, the blood flowing state in the veins below the mucous membrane of the stomach, the minute structure of the vein or the penetrated range of a tumor can be obtained. Therefore, a disease part can be diagnosed within a short time without giving an unrest to the patient or hurting the observed part.

Further, as the imaging means is provided outside the body and the observation can be made from outside the body, the size of the imaging means is not limited, a wide range can be observed and the operation is easy.

When infrared rays easy to pass through a living body are used for the above mentioned illuminating light, the transmitted light amount will increase and the observation will be easier. Further, it is known that hemoglobin in the blood absorbs infrared rays better than any other liquid or substance does and that the blood flow and the minute structure of the vein are abnormal in the stomach wall and the disease part below the mucous membrane. Much information can be obtained by using infrared rays.

The spectral characteristic and sensitivity in the illuminating light and the imaging part 5 are not limited to be of infrared rays but can be freely selected in response to the observed part and observing purpose.

Also, as the transmitted light amount is different depending on the observed part, the picture image will become bright or dark. The above mentioned camera controlling unit 6 may be provided with an automatic gain control to automatically control the picture image to be bright or dark.

Figure 3:
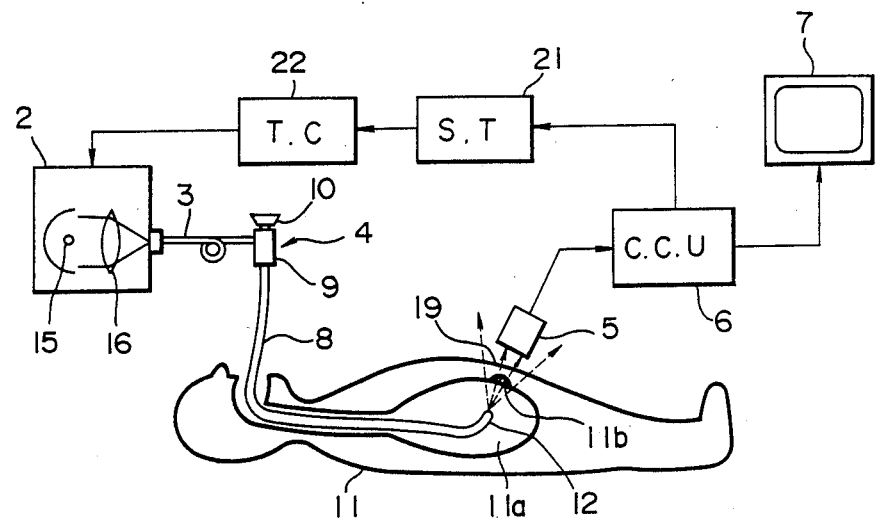
FIG. 3 is an explanatory view showing the formation of an out-body observing apparatus of the second embodiment of the present invention.

FIG. 3 is an explanatory view showing the formation of an out-body observing apparatus of the second embodiment of the present invention.

In this embodiment, the information of the received light amount in the imaging part 5 obtained in the camera controlling unit 6 is input into a timing controlling means 22 by a signal transmitting means 21 and the emitted light amount of the light source device 2 is adjusted by this timing controlling means 22. The above mentioned signal transmitting means 21 may be cordless.

According to this embodiment, as the emitted light amount of the light source device 2 can be controlled so that the received light amount of the above mentioned imaging part 5 may be substantially constant, the picture image can be kept at a substantially constant brightness and a picture image of a higher picture quality can be obtained. By a combination with the above mentioned automatic gain control, the effect can be made higher.

If the above mentioned light source device 2 is controlled to flash by the above mentioned timing control means 22, even a static picture image can have a high picture quality.

Figure 4:
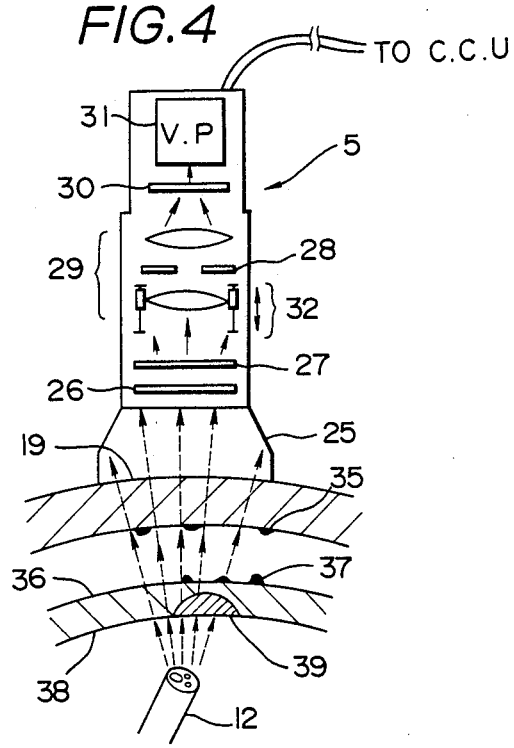
FIG. 4 is an explanatory view showing an imaging part of an out-body observing apparatus of the third embodiment of the present invention.

FIG. 4 is an explanatory view showing an imaging part of an out-body observing apparatus of the third embodiment of the present invention.

As shown in this drawing, the imaging part 5 is provided on the body surface 19 side with a mounting part 25 for keeping the distance between the imaging part 5 and body surface 19 substantially constant. This imaging part 5 is provided with a light intercepting means 26, filter 27, image forming optical system 29 including a diaphragm 28, solid state imaging device 30 and signal processing circuit 31 connected to this solid state imaging device 30 in the order mentioned from the light receiving side. Further, the above mentioned image forming optical system 29 is provided, for example, with a focus adjusting means 32 moving the lens in the optical axial direction.

The above mentioned light intercepting means 26 and filter 27 are used in case it is desired to observe an image of a light of any wavelength. The above mentioned diaphragm 28 is used to adjust the imaged field depth and received light amount.

In case the imaged field depth is deep, in FIG. 4, the image of a tumor 35 below the skin or the like, the image of a vein or tumor 37 on the outer wall 36 of the stomach or the like or the image of a tumor 39 below the mucous membrane of the inner wall 38 of the stomach or the like will be seen as overlapped and will be difficult to observe. In such a case, if any image is focused by using the above mentioned focus adjusting means 32, an image adapted for observation will be obtained. In case the illuminating light is to be switched, for example, between the infrared light and visible light, as the refractive index of the infrared light and visible light are different from each other, the focus will be displaced. However, even in such a case, the focus displacement can be compensated by using the above mentioned focus adjusting means 32.

An external irregular light can be prevented by the above mentioned mounting part 25 from entering the imaging part 5.

Parts other than the image forming optical system 29, solid state imaging device 30 and signal processing circuit 31 are used as required and therefore may be removably provided.

Figure 5:
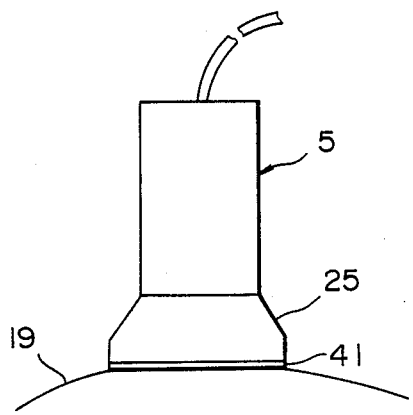
FIG. 5 is a side view showing an imaging part of an out-body observing apparatus of the fourth embodiment of the present invention.

FIG. 5 is a side view showing an imaging part of an out-body observing apparatus of the fourth embodiment of the present invention.

In this embodiment, a bonding member 41 to be bonded to the body surface 19 is provided on the tip part of the mounting part 25 of the imaging part 5.

According to this embodiment, the imaging part 5 can be fixed on the body surface 19 and the operatability is improved.

Figure 6:
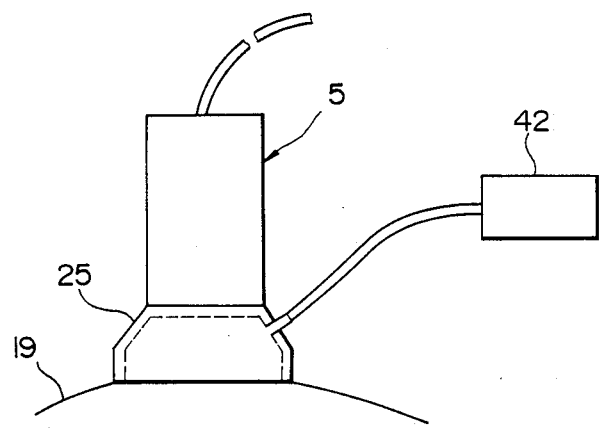
FIG. 6 is a side view showing an imaging part of an out-body observing apparatus of the fifth embodiment.

FIG. 6 is a side view showing an imaging part of an out-body observing apparatus of the fifth embodiment of the present invention.

In this embodiment, a sucking device 42 such as a vacuum pump is connected to the mounting part 25 of the imaging part 5 so as to suck air within the above mentioned mounting part 25 to fix the imaging part 5 in close contact with the body surface 19.

According to this embodiment, the operatability can be improved the same as in the above mentioned fourth embodiment and the imaging part 5 can be easily fixed and released.

Figure 7:
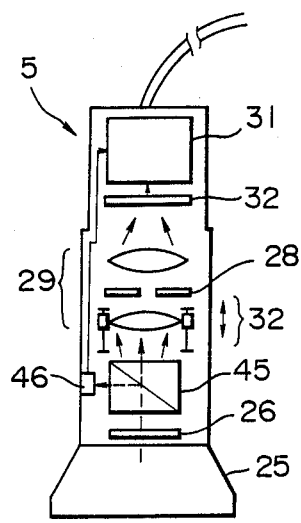
FIG. 7 is an explanatory view showing an imaging part of an out-body observing apparatus of the sixth embodiment of the present invention.

FIG. 7 is an explanatory view showing an imaging part of an out-body observing apparatus of the sixth embodiment of the present invention.

In this embodiment, a light dividing means 45 reflecting a part the incident light such as a half mirror or half prism is provided between the light intercepting means 26 and image forming optical system 29 within the imaging part 5 and also a light receiving device 46 receiving the light reflected by this light dividing means 45 is provided. The received light amount of the imaging part 5 is detected by this light receiving device 46 and the information of this received light amount is input into the camera controlling unit 6 or light source device 2 through the signal processing circuit 31 to automatically control the brightness of the picture image.

Figure 8:
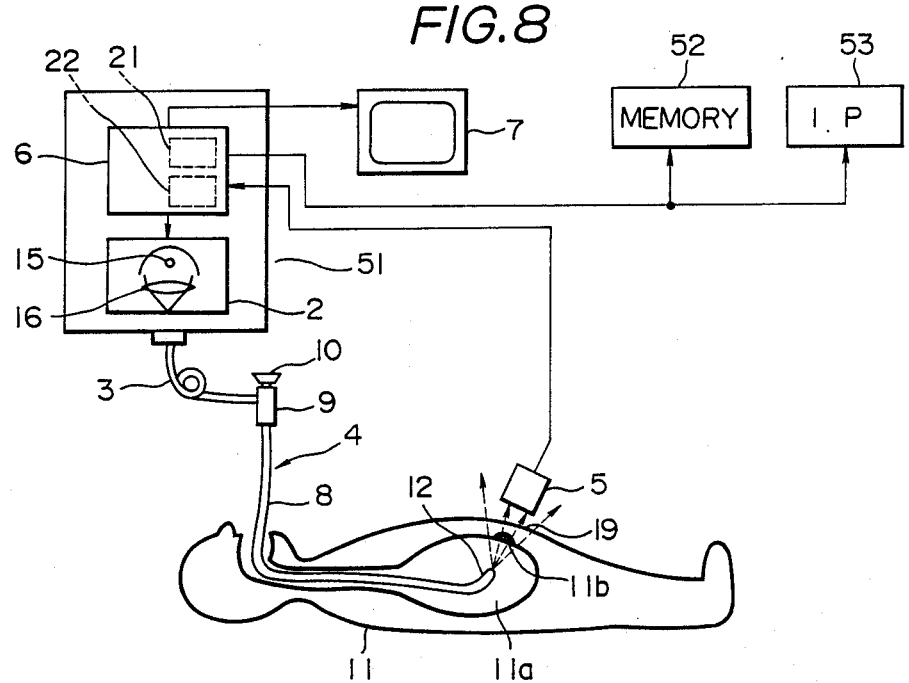
FIG. 8 is an explanatory view showing the formation of an out-body observing apparatus of the seventh embodiment of the present invention.

FIG. 8 is an explanatory view showing the formation of an out-body observing apparatus of the seventh embodiment of the present invention.

In this embodiment, the camera controlling unit 6, light source device 2, signal transmitting means 21 and timing controlling means 22 are all integrally contained within a system controller 51. Such peripheral devices as the monitor 7, an external memory means 52 and picture image processing apparatus 53 can be connected to the above mentioned system controller.

According to this embodiment, the peripheral devices can be freely or simultaneously connected and a compact observing apparatus system with high general utility can be realized.

The present invention is not limited to the above mentioned embodiment. For example, the illuminating means is not limited to be the light source device 2 and endoscope 4. Only a light emitting body such as a lamp or light emitting device may be inserted into a body cavity or a light emitting body may be provided in the tip part of the endoscope.

The imaging means using the solid state imaging device may be of a field sequential system wherein the illuminating light is sequentially switched to R (red), G (green) and B (blue) or to R, W (white) and B or a single plate system wherein a color filter is fitted to the front surface of the solid state imaging device to obtain a color picture image. Not only a solid state imaging device but also a television camera having a sensitivity to any desired wavelength range may be used for the observation. The image may be recorded on an ordinary film or infrared ray film by a still camera.

According to the above mentioned respective embodiments, an illuminating means radiating an illuminating light from within a body onto a part to be observed within the body is provided, an imaging means for observing the image of the observed part by the illuminating light of the above mentioned illuminating means having passed through a living body tissue is provided outside the body and therefore the tissue interior can be observed from outside the body.

In this invention, it is apparent that working modes different in a wide range can be formed on the basis of this invention without deviating from the spirit and scope of the invention. This invention is not restricted by its specific working mode except being limited by the appended claims.

What is claimed is:

1. An out-body observing apparatus comprising:
   an endoscope having an elongated insertable part which can be inserted into a body cavity;
   a light source device which can feed said endoscope with an illuminating light capable of illuminating the body cavity interior with light radiated from said insertable part;
   an imaging means for detecting, outside the body, light from said illuminating light fed by said light source device, radiated from said insertable part onto a part to be observed and having passed through a living body tissue, and for producing, from said detected light, a projected image of the tissue;
   a signal processing means for processing a video signal from said projected image obtained by said imaging means; and
   a displaying means which can display on a picture surface a video image of the observed part with the video signal output from said signal processing means.

2. An out-body observing apparatus according to claim 1 wherein said imaging means has a solid state imaging device which can image the projected image formed by an image forming optical system.

3. An out-body observing apparatus according claim 2 wherein said image forming optical system is provided with a focus adjusting means capable of adjusting the focus of the optical system.

4. An out-body observing apparatus according to claim 2 wherein said image forming optical system has a diaphragm.

5. An out-body observing apparatus according to claim 2 wherein said imaging means has a light dividing means in the image forming optical system.

6. An out-body observing apparatus according to claim 5 wherein said light dividing means is a half mirror or half prism.

7. An out-body observing apparatus according to claim 1 wherein said imaging means has a mounting part and has in a tip part of said mounting part a bonding member bonded to the body surface.

8. An out-body observing apparatus according to claim 1 wherein said imaging means is provided with a mounting part which can be fixed in close contact with the body surface by sucking air.

9. An out-body observing apparatus according to claim 1 wherein said light source device emits an illuminating light of one, two or all of the wavelength ranges of an ultraviolet range, visible range and infrared range.

10. An out-body observing apparatus comprising:
   an endoscope having an elongated insertable part which can be inserted into a body cavity;
   a light source device which can feed said endoscope with an illuminating light capable of illuminating the body cavity interior with light radiated from said insertable part;
   an imaging means for detecting, outside the body, light from said illuminating light fed by said light source device, radiated from said insertable part onto a part to be observed and having passed through a living body tissue, and for producing, from said detected light, a projected image of the tissue;
   a signal processing means for processing a picture image signal obtained by said imaging means to be a video signal;
   a displaying means which can display on a picture surface a video image of the observed part by the video signal output from said signal processing means; and
   an emitted light amount adjusting means for adjusting the emitted light amount of said light source device from information of the received light amount obtained by said imaging means.

11. An out-body observed apparatus according to claim 10 wherein said emitted light amount adjusting means has a signal transmitting means and timing controlling means.

12. An out-body observing apparatus according to claim 10 wherein said imaging means has a solid state imaging device which can image the optical image formed by an image forming optical system.

13. An out-body observing apparatus according to claim 12 wherein said image forming optical system is provided with a focus adjusting means capable of adjusting the focus of the optical system.

14. An out-body observing apparatus according to claim 12 wherein said image forming optical system has a diaphragm.

15. An out-body observing apparatus according to claim 10 wherein said imaging means has a mounting part and has in a tip part of said mounting part a bonding member bonded to the body surface.

16. An out-body observing apparatus according to claim 10 wherein said imaging means is provided with a mounting part which can be fixed in close contact with the body surface by sucking air.

17. An out-body observing apparatus according to claim 10 wherein said imaging means has a light dividing means in an image forming optical system that forms said projected image.

18. An out-body observing apparatus according to claim 17 wherein said light dividing means is a half mirror or half prism.

19. An out-body observing apparatus according to claim 10 wherein said light source device emits an illuminating light of one, two or all of the wavelength ranges of an ultraviolet range, visible range and infrared range.

20. An out-body observing apparatus comprising:
   an illuminating means radiating an illuminating light from within a body onto a part to be observed within said body; and
   an imaging means provided outside the body for observing the image of said part to be observed by the illuminating light of said illuminating means received by said imaging means after having passed through a living body tissue.

21. An out-body observing apparatus comprising:
   an endoscope having an elongated insertable part which can be inserted into a body cavity to illuminate interior tissue with light radiated from said insertable part;
   an imaging means for detecting, outside the body, a projected image of the interior tissue from said illuminating light radiated from said insertable part onto a part to be observed and having passed through a living body tissue and for producing a picture image signal; and
   a system controlling part provided integrally with a light source part which can feed said illuminating light, and a signal processing part for processing the picture image signal obtained by said imaging means to be a video signal.

22. An out-body observing apparatus according to claim 21 wherein said system controlling part has a signal transmitting means whereby the emitted light amount of the light source part can be adjusted by the information of the received slight amount obtained from the imaging means and a timing controlling means.

23. An out-body observing apparatus according to claim 22 wherein said imaging means has a light dividing means in the image forming optical system.

24. An out-body observing apparatus according to claim 23 wherein said light dividing means is a half mirror or half prism.

25. An out-body observing apparatus according to claim 21 wherein said imaging means has a solid state imaging device which can image the optical image formed by an image forming optical system.

26. An out-body observing apparatus according to claim 25 wherein said image forming optical system is provided with a focus adjusting means capable of adjusting the focus of the optical system.

27. An out-body observing apparatus according to claim 25 wherein said image forming optical system has a diaphragm.

28. An out-body observing apparatus according to claim 21 wherein said imaging means has a mounting part and has in a tip part of said mounting part a bonding member bonded to the body surface.

29. An out-body observing apparatus according to claim 21 wherein said imaging means is provided with a mounting part which can be fixed in close contact with the body surface by sucking air.

30. An out-body observing apparatus according to claim 21 wherein said light source device emits an illuminating light of one, two or all of the wavelength ranges of an ultraviolet range, visible range and infrared range.

* * * * *